(12) United States Patent
Bicknell et al.

(10) Patent No.: US 8,668,670 B2
(45) Date of Patent: Mar. 11, 2014

(54) AUTOMATIC INJECTION DEVICES (75) Inventors: Stephen Bicknell, Warwickshire (GB);
Joseph F. Julian, Libertyville, IL (US);
William L. Rudzena, Johnsburg, IL (US)

(73) Assignee: Abbvie Biotechnology Ltd, Hamilton (BM)

( * ) Notice: Subject to any disclaimer, the term of this patent is extended or adjusted under 35 U.S.C. 154(b) by 0 days.

(21) Appl. No.: 13/443,384

(22) Filed: Apr. 10, 2012

(65) Prior Publication Data

US 2012/0197209 A1    Aug. 2, 2012

Related U.S. Application Data

(63) Continuation of application No. 13/072,289, filed on Mar. 25, 2011, now Pat. No. 8,162,887, which is a continuation of application No. 11/630,507, filed as application No. PCT/GB2005/002487 on Jun. 23, 2005, now Pat. No. 7,938,802.

(30) Foreign Application Priority Data

Jun. 23, 2004  (GB) .................................. 0414054

(51) Int. Cl.
*A61M 5/20*    (2006.01)
(52) U.S. Cl.
USPC ........................................................ 604/135
(58) Field of Classification Search
USPC ............................. 604/136, 157, 164.12, 135
See application file for complete search history.

(56) References Cited

U.S. PATENT DOCUMENTS

| | | | |
|---|---|---|---|
| 2,398,544 A | 4/1946 | Lockhart | |
| 2,459,875 A | 1/1949 | Folkman | |
| 2,565,081 A | 8/1951 | Maynes | |
| 2,591,457 A | 4/1952 | Maynes | |
| 2,701,566 A | 2/1955 | Krug | |
| 2,888,924 A | 6/1956 | Dunmire | |
| 2,752,918 A | 7/1956 | Uytenbogaart | |
| 2,832,339 A * | 4/1958 | Sarnoff et al. | ................ 604/138 |
| 2,960,087 A | 11/1960 | Uytenbogaart | |
| 3,051,173 A | 8/1962 | Johnson et al. | |

(Continued)

FOREIGN PATENT DOCUMENTS

| | | | |
|---|---|---|---|
| CA | 2741354 A1 | 4/2010 | |
| DE | 2019296 A1 | 11/1971 | |

(Continued)

OTHER PUBLICATIONS

Examination Report issued in New Zealand Application No. 595605, dated Apr. 12, 2013.

(Continued)

*Primary Examiner* — Nicholas Lucchesi
*Assistant Examiner* — Diva K Chander
(74) *Attorney, Agent, or Firm* — McCarter & English, LLP; David R. Burns (57) ABSTRACT

An injection device comprises a syringe extendible against a spring bias from a retracted position in a housing to a projecting injecting position. A spring biased plunger has collapsible elbows which, when the plunger is released, initially engage the end of the syringe to drive it to the projecting position, whereupon arresting of the syringe movement causes the elbows to collapse inside the syringe to allow the plunger to engage and drive the bung.

17 Claims, 1 Drawing Sheet

(56) References Cited

U.S. PATENT DOCUMENTS

| | | | |
|---|---|---|---|
| 3,055,362 A | 9/1962 | Uytenbogaart |
| 3,066,670 A | 12/1962 | Stauffer |
| 3,136,313 A | 6/1964 | Enstrom et al. |
| 3,314,428 A | 4/1967 | Johnson et al. |
| 3,330,279 A | 7/1967 | Sarnoff et al. |
| 3,403,680 A | 10/1968 | Sinclair et al. |
| 3,496,937 A | 2/1970 | Fletcher |
| 3,541,663 A | 11/1970 | Szpur |
| 3,543,603 A | 12/1970 | Gley |
| 3,605,743 A | 9/1971 | Arce |
| 3,618,603 A | 11/1971 | Levenson |
| 3,702,609 A | 11/1972 | Steiner |
| 3,712,301 A | 1/1973 | Sarnoff |
| 3,742,948 A | 7/1973 | Post et al. |
| 3,797,488 A | 3/1974 | Hurschman et al. |
| 3,797,489 A | 3/1974 | Sarnoff |
| 3,882,863 A | 5/1975 | Sarnoff et al. |
| 3,892,237 A | 7/1975 | Steiner |
| 3,910,260 A | 10/1975 | Sarnoff et al. |
| 3,941,130 A | 3/1976 | Tibbs |
| 4,004,577 A | 1/1977 | Sarnoff |
| 4,031,893 A | 6/1977 | Kaplan et al. |
| 4,106,770 A | 8/1978 | Gray |
| 4,178,928 A | 12/1979 | Tischlinger |
| 4,202,314 A | 5/1980 | Smirnov et al. |
| 4,214,584 A | 7/1980 | Smirnov et al. |
| 4,226,235 A | 10/1980 | Sarnoff et al. |
| 4,258,713 A | 3/1981 | Wardlaw |
| 4,261,358 A | 4/1981 | Vargas et al. |
| 4,275,729 A | 6/1981 | Silver et al. |
| 4,394,863 A | 7/1983 | Bartner |
| 4,399,216 A | 8/1983 | Axel et al. |
| 4,425,120 A | 1/1984 | Sampson et al. |
| 4,437,859 A | 3/1984 | Whitehouse et al. |
| 4,447,231 A | 5/1984 | Bekkering |
| 4,510,245 A | 4/1985 | Cousens et al. |
| 4,530,695 A | 7/1985 | Phillips et al. |
| 4,565,543 A | 1/1986 | Bekkering et al. |
| 4,573,976 A | 3/1986 | Sampson et al. |
| 4,578,064 A | 3/1986 | Sarnoff et al. |
| 4,610,254 A | 9/1986 | Morgan et al. |
| 4,619,265 A | 10/1986 | Morgan et al. |
| 4,624,660 A | 11/1986 | Mijers et al. |
| 4,634,665 A | 1/1987 | Axel et al. |
| 4,637,403 A | 1/1987 | Garcia et al. |
| 4,640,686 A | 2/1987 | Dalling et al. |
| 4,664,653 A | 5/1987 | Sagstetter et al. |
| 4,678,461 A | 7/1987 | Mesa |
| 4,689,042 A | 8/1987 | Sarnoff et al. |
| 4,723,937 A | 2/1988 | Sarnoff et al. |
| 4,755,169 A | 7/1988 | Sarnoff et al. |
| 4,795,432 A | 1/1989 | Karczmer |
| 4,795,433 A | 1/1989 | Sarnoff |
| 4,816,397 A | 3/1989 | Boss et al. |
| 4,816,567 A | 3/1989 | Cabilly et al. |
| 4,820,286 A | 4/1989 | van der Wal |
| 4,822,340 A | 4/1989 | Kamstra |
| 4,850,994 A | 7/1989 | Zerbst et al. |
| 4,852,768 A | 8/1989 | Bartsch |
| 4,902,279 A | 2/1990 | Schmidtz et al. |
| 4,923,447 A | 5/1990 | Morgan |
| 4,927,416 A | 5/1990 | Tomkiel |
| 4,929,237 A | 5/1990 | Medway |
| 4,955,868 A | 9/1990 | Klein |
| 4,966,592 A | 10/1990 | Burns et al. |
| 4,968,615 A | 11/1990 | Koszinowski et al. |
| 4,994,034 A | 2/1991 | Botich et al. |
| 5,041,088 A | 8/1991 | Ritson et al. |
| 5,042,977 A | 8/1991 | Bechtold et al. |
| 5,049,133 A | 9/1991 | Villen |
| D322,479 S | 12/1991 | Miyaguchi |
| 5,071,353 A | 12/1991 | van der Wal |
| 5,085,641 A | 2/1992 | Sarnoff et al. |
| 5,085,642 A | 2/1992 | Sarnoff et al. |
| 5,092,842 A | 3/1992 | Bechtold et al. |
| 5,092,843 A | 3/1992 | Monroe et al. |
| 5,102,393 A | 4/1992 | Sarnoff et al. |
| 5,104,380 A | 4/1992 | Holman et al. |
| 5,114,406 A | 5/1992 | Gabriel et al. |
| 5,114,410 A | 5/1992 | Batlle |
| 5,137,516 A | 8/1992 | Rand et al. |
| 5,163,918 A | 11/1992 | Righi et al. |
| 5,168,062 A | 12/1992 | Stinski |
| 5,179,017 A | 1/1993 | Axel et al. |
| 5,201,708 A | 4/1993 | Martin |
| 5,223,409 A | 6/1993 | Ladner et al. |
| 5,224,936 A | 7/1993 | Gallagher |
| 5,225,539 A | 7/1993 | Winter |
| 5,231,024 A | 7/1993 | Moeller et al. |
| 5,242,240 A | 9/1993 | Gorham |
| 5,244,465 A | 9/1993 | Michel |
| 5,259,840 A | 11/1993 | Boris |
| 5,263,934 A | 11/1993 | Haak |
| 5,267,963 A | 12/1993 | Bachynsky |
| 5,267,972 A | 12/1993 | Anderson |
| 5,267,976 A | 12/1993 | Guerineau et al. |
| 5,273,544 A | 12/1993 | van der Wal |
| D343,897 S | 2/1994 | Rand et al. |
| 5,295,965 A | 3/1994 | Wilmot |
| 5,295,975 A | 3/1994 | Lockwood, Jr. |
| 5,298,024 A * | 3/1994 | Richmond ............ 604/90 |
| D346,219 S | 4/1994 | Fardigh |
| 5,300,030 A * | 4/1994 | Crossman et al. ......... 604/136 |
| 5,318,538 A | 6/1994 | Martin |
| 5,320,609 A | 6/1994 | Haber et al. |
| 5,334,144 A | 8/1994 | Alchas et al. |
| 5,342,308 A | 8/1994 | Boschetti |
| 5,346,480 A | 9/1994 | Hess et al. |
| 5,358,489 A | 10/1994 | Wyrick |
| 5,376,080 A | 12/1994 | Petrussa |
| 5,378,233 A | 1/1995 | Haber et al. |
| 5,383,864 A | 1/1995 | van den Heuvel |
| 5,383,865 A | 1/1995 | Michel |
| 5,391,151 A * | 2/1995 | Wilmot ............... 604/139 |
| 5,425,715 A | 6/1995 | Dalling et al. |
| 5,433,712 A | 7/1995 | Stiles et al. |
| 5,478,316 A | 12/1995 | Bitdinger et al. |
| 5,480,387 A | 1/1996 | Gabriel et al. |
| 5,530,101 A | 6/1996 | Queen et al. |
| 5,531,705 A | 7/1996 | Alter et al. |
| 5,567,160 A | 10/1996 | Massino |
| 5,569,192 A | 10/1996 | van der Wal |
| 5,585,089 A | 12/1996 | Queen et al. |
| 5,591,138 A | 1/1997 | Vaillancourt |
| 5,599,309 A | 2/1997 | Marshall et al. |
| 5,599,314 A | 2/1997 | Neill |
| 5,616,128 A | 4/1997 | Meyer |
| 5,620,421 A | 4/1997 | Schmitz |
| 5,634,906 A | 6/1997 | Haber et al. |
| 5,637,094 A | 6/1997 | Stewart, Jr. et al. |
| 5,645,534 A | 7/1997 | Chanoch |
| 5,645,571 A | 7/1997 | Olson et al. |
| 5,656,272 A | 8/1997 | Le et al. |
| 5,658,259 A | 8/1997 | Pearson et al. |
| 5,681,291 A | 10/1997 | Galli |
| 5,693,761 A | 12/1997 | Queen et al. |
| 5,693,762 A | 12/1997 | Queen et al. |
| 5,744,360 A | 4/1998 | Hu et al. |
| 5,779,677 A | 7/1998 | Frezza |
| 5,792,190 A | 8/1998 | Olson et al. |
| 5,797,969 A | 8/1998 | Olson et al. |
| 5,807,335 A | 9/1998 | Kriesel et al. |
| 5,807,346 A | 9/1998 | Frezza |
| 5,817,111 A | 10/1998 | Riza |
| 5,843,036 A | 12/1998 | Olive et al. |
| 5,845,644 A | 12/1998 | Hughes et al. |
| 5,860,957 A | 1/1999 | Jacobsen et al. |
| 5,885,250 A | 3/1999 | Kriesel et al. |
| 5,919,212 A | 7/1999 | Olson et al. |
| 5,931,817 A | 8/1999 | Nguyen et al. |
| 5,957,886 A | 9/1999 | Weston |
| 5,957,897 A | 9/1999 | Jeffrey |
| 5,984,900 A | 11/1999 | Mikkelsen |
| 5,993,421 A | 11/1999 | Kriesel |

(56) References Cited

U.S. PATENT DOCUMENTS

| | | | |
|---|---|---|---|
| 6,048,336 A | 4/2000 | Gabriel |
| 6,056,728 A | 5/2000 | von Schuckmann |
| 6,077,247 A | 6/2000 | Marshall et al. |
| D428,651 S | 7/2000 | Andersson et al. |
| 6,090,070 A | 7/2000 | Hager et al. |
| 6,090,080 A | 7/2000 | Jost et al. |
| 6,090,382 A | 7/2000 | Salfeld et al. |
| 6,099,503 A | 8/2000 | Stradella |
| 6,102,896 A | 8/2000 | Roser |
| 6,110,147 A | 8/2000 | Perouse |
| 6,125,299 A | 9/2000 | Groenke et al. |
| 6,149,626 A | 11/2000 | Bachynsky et al. |
| 6,159,181 A | 12/2000 | Crossman et al. |
| 6,171,285 B1 | 1/2001 | Johnson |
| 6,203,530 B1 | 3/2001 | Stewart, Sr. |
| 6,210,369 B1 | 4/2001 | Wilmot et al. |
| 6,213,987 B1 | 4/2001 | Hirsch et al. |
| 6,221,044 B1 | 4/2001 | Greco |
| 6,241,709 B1 | 6/2001 | Bechtold et al. |
| 6,258,068 B1 | 7/2001 | Kirchhofer et al. |
| 6,258,562 B1 | 7/2001 | Salfeld et al. |
| 6,270,479 B1 | 8/2001 | Bergens et al. |
| 6,277,097 B1 | 8/2001 | Mikkelsen et al. |
| 6,277,098 B1 | 8/2001 | Klitmose et al. |
| 6,277,099 B1 | 8/2001 | Strowe et al. |
| 6,280,421 B1 | 8/2001 | Kirchhofer et al. |
| 6,312,412 B1 | 11/2001 | Saied et al. |
| 6,319,011 B1 | 11/2001 | Motti et al. |
| 6,319,233 B1 | 11/2001 | Jansen et al. |
| 6,319,234 B1 | 11/2001 | Restelli et al. |
| 6,322,540 B1 | 11/2001 | Grabis et al. |
| 6,325,066 B1 | 12/2001 | Hughes et al. |
| 6,328,699 B1 | 12/2001 | Eigler et al. |
| 6,334,070 B1 | 12/2001 | Nova et al. |
| D453,569 S | 2/2002 | Himbert |
| 6,371,939 B2 | 4/2002 | Bergens et al. |
| 6,387,074 B1 | 5/2002 | Horppu et al. |
| 6,387,078 B1 | 5/2002 | Gillespie, III |
| 6,413,237 B1 | 7/2002 | Caizza et al. |
| 6,419,658 B1 | 7/2002 | Restelli et al. |
| D461,555 S | 8/2002 | Binet et al. |
| 6,448,380 B2 | 9/2002 | Rathjen et al. |
| 6,451,983 B2 | 9/2002 | Rathjen et al. |
| 6,454,746 B1 | 9/2002 | Bydlon et al. |
| 6,475,194 B2 | 11/2002 | Domici, Jr. et al. |
| 6,498,237 B2 | 12/2002 | Rathjen et al. |
| 6,502,699 B1 | 1/2003 | Watson |
| 6,509,015 B1 | 1/2003 | Salfeld et al. |
| 6,517,517 B1 | 2/2003 | Farrugia et al. |
| 6,544,234 B1 | 4/2003 | Gabriel |
| 6,575,939 B1 | 6/2003 | Brunel |
| 6,589,210 B1 | 7/2003 | Rolfe |
| 6,593,458 B1 | 7/2003 | Rathjen et al. |
| 6,656,163 B1 | 12/2003 | Marshall et al. |
| 6,656,164 B1 | 12/2003 | Smith |
| 6,673,035 B1 | 1/2004 | Rice et al. |
| 6,692,469 B1 | 2/2004 | Weekes et al. |
| 6,697,671 B1 | 2/2004 | Nova et al. |
| 6,712,788 B2 | 3/2004 | Righi et al. |
| 6,743,203 B1 | 6/2004 | Pickhard |
| 6,752,798 B2 | 6/2004 | McWethy et al. |
| 6,767,336 B1 | 7/2004 | Kaplan |
| D494,270 S | 8/2004 | Reschke |
| 6,773,415 B2 | 8/2004 | Heiniger |
| 6,796,967 B2 | 9/2004 | Jensen |
| 6,802,827 B2 | 10/2004 | Andersson |
| 6,805,686 B1 | 10/2004 | Fathallah et al. |
| 6,808,507 B2 | 10/2004 | Roser |
| 6,817,989 B2 | 11/2004 | Svendsen et al. |
| 6,872,080 B2 | 3/2005 | Pastrick et al. |
| 6,872,194 B2 | 3/2005 | Doyle et al. |
| 6,926,697 B2 | 8/2005 | Malenchek |
| 6,932,793 B1 | 8/2005 | Marshall et al. |
| 6,945,960 B2 | 9/2005 | Barker et al. |
| 6,969,259 B2 | 11/2005 | Pastrick et al. |
| 6,970,742 B2 | 11/2005 | Mann et al. |
| 6,976,976 B2 | 12/2005 | Doyle |
| 6,986,760 B2 | 1/2006 | Giambattista et al. |
| 7,004,929 B2 | 2/2006 | McWethy et al. |
| D518,175 S | 3/2006 | Hardin, Jr. et al. |
| 7,056,306 B1 | 6/2006 | Halseth et al. |
| 7,115,095 B2 | 10/2006 | Eigler et al. |
| 7,137,953 B2 | 11/2006 | Eigler et al. |
| 7,223,394 B2 | 5/2007 | Salfeld et al. |
| D545,439 S | 6/2007 | Draudt et al. |
| 7,320,682 B2 | 1/2008 | Cocker et al. |
| 7,361,160 B2 | 4/2008 | Hommann et al. |
| 7,416,540 B2 | 8/2008 | Edwards et al. |
| 7,483,743 B2 | 1/2009 | Mann et al. |
| 7,497,847 B2 | 3/2009 | Crawford et al. |
| 7,541,031 B2 | 6/2009 | Salfeld et al. |
| 7,588,761 B2 | 9/2009 | Salfeld et al. |
| 7,590,449 B2 | 9/2009 | Mann et al. |
| 7,648,482 B2 | 1/2010 | Edwards et al. |
| 7,648,483 B2 | 1/2010 | Edwards et al. |
| 7,682,155 B2 | 3/2010 | Raven et al. |
| 7,694,828 B2 | 4/2010 | Swift et al. |
| 7,717,854 B2 | 5/2010 | Mann et al. |
| 7,731,686 B2 | 6/2010 | Edwards et al. |
| 7,731,690 B2 | 6/2010 | Edwards et al. |
| 7,736,333 B2 * | 6/2010 | Gillespie, III ................. 604/110 |
| D619,702 S | 7/2010 | Galbraith |
| 7,749,194 B2 | 7/2010 | Edwards et al. |
| D621,932 S | 8/2010 | Sonleiter et al. |
| D622,374 S | 8/2010 | Julian et al. |
| 7,771,397 B1 | 8/2010 | Olson |
| D628,690 S | 12/2010 | Galbraith |
| D629,098 S | 12/2010 | Sonleiter et al. |
| D629,509 S | 12/2010 | Julian et al. |
| 7,863,426 B2 | 1/2011 | Wan et al. |
| D633,199 S | 2/2011 | MacKay et al. |
| 7,918,823 B2 | 4/2011 | Edwards et al. |
| 7,919,264 B2 | 4/2011 | Maksymowych et al. |
| D638,935 S | 5/2011 | Gilmore, III et al. |
| 7,938,802 B2 | 5/2011 | Bicknell et al. |
| 7,947,017 B2 | 5/2011 | Edwards et al. |
| D641,077 S | 7/2011 | Sanders et al. |
| D645,139 S | 9/2011 | Sawhney et al. |
| 8,016,788 B2 | 9/2011 | Edwards et al. |
| 8,021,344 B2 | 9/2011 | Edwards et al. |
| D647,613 S | 10/2011 | Paget et al. |
| 8,069,097 B2 | 11/2011 | Patrick et al. |
| D650,070 S | 12/2011 | Mori |
| D653,329 S | 1/2012 | Lee-Sepsick |
| 8,105,281 B2 | 1/2012 | Edwards et al. |
| 8,123,719 B2 | 2/2012 | Edwards et al. |
| 8,162,887 B2 | 4/2012 | Bicknell et al. |
| 8,172,082 B2 | 5/2012 | Edwards et al. |
| 8,206,360 B2 | 6/2012 | Edwards et al. |
| 8,226,610 B2 | 7/2012 | Edwards et al. |
| 8,231,573 B2 | 7/2012 | Edwards et al. |
| 8,313,466 B2 | 11/2012 | Edwards et al. |
| 8,361,026 B2 | 1/2013 | Edwards et al. |
| 8,372,030 B2 | 2/2013 | Dixon et al. |
| D677,380 S | 3/2013 | Julian et al. |
| 8,425,462 B2 | 4/2013 | Edwards et al. |
| 2001/0005781 A1 | 6/2001 | Bergens et al. |
| 2001/0025168 A1 | 9/2001 | Gross et al. |
| 2001/0053894 A1 | 12/2001 | Steenfeldt-Jensen et al. |
| 2002/0002344 A1 | 1/2002 | Douglas et al. |
| 2002/0016563 A1 | 2/2002 | Hill et al. |
| 2002/0042592 A1 | 4/2002 | Wilmot et al. |
| 2002/0095120 A1 | 7/2002 | Larsen et al. |
| 2002/0111587 A1 | 8/2002 | Hommann et al. |
| 2002/0161337 A1 | 10/2002 | Shaw et al. |
| 2002/0169408 A1 | 11/2002 | Beretta et al. |
| 2002/0183690 A1 | 12/2002 | Arnisolle |
| 2003/0004466 A1 | 1/2003 | Bitdinger et al. |
| 2003/0004467 A1 | 1/2003 | Musick et al. |
| 2003/0012786 A1 | 1/2003 | Teoh et al. |
| 2003/0023203 A1 | 1/2003 | Lavi et al. |
| 2003/0023205 A1 | 1/2003 | Botich et al. |
| 2003/0050606 A1 | 3/2003 | Brand et al. |
| 2003/0055345 A1 | 3/2003 | Eigler et al. |

(56) References Cited

U.S. PATENT DOCUMENTS

| | | |
|---|---|---|
| 2003/0092059 A1 | 5/2003 | Salfeld et al. |
| 2003/0093036 A1 | 5/2003 | Crossman et al. |
| 2003/0099358 A1 | 5/2003 | Michael et al. |
| 2003/0105430 A1 | 6/2003 | Lavi et al. |
| 2003/0153868 A1 | 8/2003 | Azizi et al. |
| 2003/0161744 A1 | 8/2003 | Vilks et al. |
| 2003/0161828 A1 | 8/2003 | Abdelghany et al. |
| 2003/0187401 A1 | 10/2003 | Doyle |
| 2003/0206898 A1 | 11/2003 | Fischkoff et al. |
| 2003/0212362 A1 | 11/2003 | Roser |
| 2003/0216785 A1 | 11/2003 | Edwards et al. |
| 2003/0219438 A1 | 11/2003 | Salfeld et al. |
| 2003/0229308 A1 | 12/2003 | Tsals et al. |
| 2003/0235585 A1 | 12/2003 | Fischkoff et al. |
| 2003/0236502 A1 | 12/2003 | De La Serna et al. |
| 2004/0009172 A1 | 1/2004 | Fischkoff et al. |
| 2004/0019326 A1 | 1/2004 | Gilbert et al. |
| 2004/0024367 A1 | 2/2004 | Gilbert |
| 2004/0033228 A1 | 2/2004 | Krause et al. |
| 2004/0039336 A1 | 2/2004 | Amark et al. |
| 2004/0039337 A1 | 2/2004 | Letzing |
| 2004/0054327 A1 | 3/2004 | Gillespie |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0143298 A1 | 7/2004 | Nova et al. |
| 2004/0147875 A1 | 7/2004 | Wallace et al. |
| 2004/0151722 A1 | 8/2004 | Banerjee et al. |
| 2004/0166111 A1 | 8/2004 | Kaymakcalan et al. |
| 2004/0199117 A1 | 10/2004 | Giambattista et al. |
| 2004/0215151 A1 | 10/2004 | Marshall et al. |
| 2004/0219142 A1 | 11/2004 | Banerjee et al. |
| 2004/0225262 A1 | 11/2004 | Fathallah et al. |
| 2004/0229854 A1 | 11/2004 | Haan De |
| 2005/0020979 A1 | 1/2005 | Westbye et al. |
| 2005/0020984 A1 | 1/2005 | Lesch |
| 2005/0027255 A1 | 2/2005 | Lavi et al. |
| 2005/0049550 A1 | 3/2005 | Kirchhofer et al. |
| 2005/0049561 A1 | 3/2005 | Hommann et al. |
| 2005/0085776 A1 | 4/2005 | Hommann et al. |
| 2005/0090647 A1 | 4/2005 | Gatanaga et al. |
| 2005/0095208 A1 | 5/2005 | Battaglia et al. |
| 2005/0096597 A1 | 5/2005 | Crawford et al. |
| 2005/0101919 A1 | 5/2005 | Brunnberg |
| 2005/0115508 A1 | 6/2005 | Little |
| 2005/0124940 A1 | 6/2005 | Martin et al. |
| 2005/0137196 A1 | 6/2005 | Timmer et al. |
| 2005/0137534 A1 | 6/2005 | Hommann |
| 2005/0137571 A1 | 6/2005 | Hommann |
| 2005/0165360 A1 | 7/2005 | Stamp |
| 2005/0165361 A1 | 7/2005 | Marshall et al. |
| 2005/0165362 A1 | 7/2005 | Slawson |
| 2005/0165363 A1 | 7/2005 | Judson et al. |
| 2005/0171476 A1 | 8/2005 | Judson et al. |
| 2005/0171477 A1 | 8/2005 | Rubin et al. |
| 2005/0209569 A1 | 9/2005 | Ishikawa et al. |
| 2005/0222539 A1 | 10/2005 | Gonzales et al. |
| 2005/0222540 A1 | 10/2005 | Kirchhofer et al. |
| 2005/0261634 A1 | 11/2005 | Karlsson |
| 2005/0261742 A1 | 11/2005 | Nova et al. |
| 2005/0273054 A1 | 12/2005 | Asch |
| 2005/0273055 A1 | 12/2005 | Harrison et al. |
| 2005/0273061 A1 | 12/2005 | Hommann et al. |
| 2005/0277885 A1 | 12/2005 | Scherer |
| 2005/0277886 A1 | 12/2005 | Hommann et al. |
| 2005/0277893 A1 | 12/2005 | Liversidge |
| 2005/0288633 A1 | 12/2005 | Jeffrey |
| 2006/0009385 A1 | 1/2006 | Hoffman et al. |
| 2006/0009810 A1 | 1/2006 | Mann et al. |
| 2006/0024293 A1 | 2/2006 | Salfeld et al. |
| 2006/0030819 A1 | 2/2006 | Young et al. |
| 2006/0036216 A1 | 2/2006 | Rimlinger et al. |
| 2006/0047250 A1 | 3/2006 | Hickingbotham et al. |
| 2006/0058848 A1 | 3/2006 | Piraino et al. |
| 2006/0069350 A1 | 3/2006 | Buenger et al. |
| 2006/0069354 A1 | 3/2006 | Buenger et al. |
| 2006/0074519 A1 | 4/2006 | Barker et al. |
| 2006/0083741 A1 | 4/2006 | Hoffman et al. |
| 2006/0089540 A1 | 4/2006 | Meissner |
| 2006/0100588 A1 | 5/2006 | Brunnberg et al. |
| 2006/0111666 A1 | 5/2006 | Hommann et al. |
| 2006/0111674 A1 | 5/2006 | Vedrine |
| 2006/0129122 A1 | 6/2006 | Wyrick |
| 2006/0140907 A1 | 6/2006 | Blumberg et al. |
| 2006/0153846 A1 | 7/2006 | Krause et al. |
| 2006/0167413 A1 | 7/2006 | Marshall et al. |
| 2006/0178865 A1 | 8/2006 | Edwards et al. |
| 2006/0189933 A1 | 8/2006 | Alheidt et al. |
| 2006/0204939 A1 | 9/2006 | Bardsley et al. |
| 2006/0253083 A1 | 11/2006 | Liu |
| 2007/0032831 A1 | 2/2007 | Eigler et al. |
| 2007/0041905 A1 | 2/2007 | Hoffman et al. |
| 2007/0049865 A1 | 3/2007 | Radmer et al. |
| 2007/0071747 A1 | 3/2007 | Hoffman et al. |
| 2007/0081996 A1 | 4/2007 | Hoffman et al. |
| 2007/0088223 A1 | 4/2007 | Mann et al. |
| 2007/0129674 A1 | 6/2007 | Liversidge |
| 2007/0129708 A1 | 6/2007 | Edwards et al. |
| 2007/0142776 A9 | 6/2007 | Kovelman et al. |
| 2007/0161960 A1 | 7/2007 | Chen et al. |
| 2007/0172897 A1 | 7/2007 | Maksymowych et al. |
| 2007/0173772 A1 | 7/2007 | Liversidge |
| 2007/0197976 A1 | 8/2007 | Jacobs et al. |
| 2007/0202104 A1 | 8/2007 | Banerjee et al. |
| 2007/0239117 A1 | 10/2007 | Chelak et al. |
| 2007/0249813 A1 | 10/2007 | Salfeld et al. |
| 2007/0292442 A1 | 12/2007 | Wan et al. |
| 2008/0019969 A1 | 1/2008 | Gorman |
| 2008/0059133 A1 | 3/2008 | Edwards et al. |
| 2008/0097337 A1 | 4/2008 | Judd et al. |
| 2008/0103490 A1 | 5/2008 | Edwards et al. |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banerjee et al. |
| 2008/0208125 A1 | 8/2008 | Bicknell et al. |
| 2008/0208140 A1 | 8/2008 | Barrelle |
| 2008/0227136 A1 | 9/2008 | Pla et al. |
| 2008/0269689 A1 | 10/2008 | Edwards et al. |
| 2008/0269692 A1 | 10/2008 | James et al. |
| 2008/0300549 A1 | 12/2008 | Verespej et al. |
| 2008/0311043 A1 | 12/2008 | Hoffman et al. |
| 2009/0017472 A1 | 1/2009 | Stuhlmuller et al. |
| 2009/0024076 A1 | 1/2009 | Babaev |
| 2009/0024093 A1 | 1/2009 | Carrel et al. |
| 2009/0024112 A1 | 1/2009 | Edwards et al. |
| 2009/0028794 A1 | 1/2009 | Medich et al. |
| 2009/0036870 A1 | 2/2009 | Mounce et al. |
| 2009/0093792 A1 | 4/2009 | Gross et al. |
| 2009/0110679 A1 | 4/2009 | Li et al. |
| 2009/0123378 A1 | 5/2009 | Wong et al. |
| 2009/0148513 A1 | 6/2009 | Fraunhofer et al. |
| 2009/0155205 A1 | 6/2009 | Salfeld et al. |
| 2009/0157012 A1 | 6/2009 | Magne |
| 2009/0182284 A1 | 7/2009 | Morgan |
| 2009/0226530 A1 | 9/2009 | Lassner et al. |
| 2009/0239259 A1 | 9/2009 | Hsieh |
| 2009/0240195 A1 | 9/2009 | Schrul et al. |
| 2009/0240210 A1 | 9/2009 | Walton et al. |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0299328 A1 | 12/2009 | Mudd et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong |
| 2010/0022963 A1 | 1/2010 | Edwards et al. |
| 2010/0034823 A1 | 2/2010 | Borhani et al. |

(56) References Cited

U.S. PATENT DOCUMENTS

| | | |
|---|---|---|
| 2010/0040604 A1 | 2/2010 | Salfeld et al. |
| 2010/0040630 A1 | 2/2010 | Elden et al. |
| 2010/0121276 A1 | 5/2010 | Edwards et al. |
| 2010/0160869 A1 | 6/2010 | Liversidge |
| 2010/0160894 A1 | 6/2010 | Julian et al. |
| 2010/0211005 A1 | 8/2010 | Edwards et al. |
| 2010/0241075 A1 | 9/2010 | Edwards et al. |
| 2010/0278822 A1 | 11/2010 | Fraunhofer et al. |
| 2010/0309012 A1 | 12/2010 | Edwards et al. |
| 2010/0318035 A1 | 12/2010 | Edwards et al. |
| 2011/0002935 A1 | 1/2011 | Wan et al. |
| 2011/0054414 A1 | 3/2011 | Shang et al. |
| 2011/0171227 A1 | 7/2011 | Okun et al. |
| 2011/0178500 A1 | 7/2011 | Shang et al. |
| 2011/0300151 A1 | 12/2011 | Okun et al. |
| 2011/0319822 A1 | 12/2011 | Edwards et al. |
| 2012/0008811 A1 | 1/2012 | Edwards et al. |
| 2012/0014956 A1 | 1/2012 | Kupper et al. |
| 2012/0015335 A1 | 1/2012 | Smith et al. |
| 2012/0022499 A1 | 1/2012 | Anderson et al. |
| 2012/0071829 A1 | 3/2012 | Edwards et al. |
| 2012/0107783 A1 | 5/2012 | Julian et al. |
| 2012/0116318 A1 | 5/2012 | Edwards et al. |
| 2012/0129185 A1 | 5/2012 | Maksymowych et al. |
| 2012/0233834 A1 | 9/2012 | Szechinski et al. |
| 2012/0238961 A1 | 9/2012 | Julian et al. |
| 2012/0289905 A1 | 11/2012 | Julian et al. |

FOREIGN PATENT DOCUMENTS

| | | | |
|---|---|---|---|
| DE | 19821933 C1 | 11/1999 | |
| DE | 60207576 T2 | 6/2006 | |
| EP | 0068864 A2 | 1/1983 | |
| EP | 0125023 A1 | 11/1984 | |
| EP | 0154316 A2 | 9/1985 | |
| EP | 0171496 A2 | 2/1986 | |
| EP | 0173494 A2 | 3/1986 | |
| EP | 0184187 A2 | 6/1986 | |
| EP | 0260610 A2 | 3/1988 | |
| EP | 0401384 A1 | 12/1990 | |
| EP | 1334740 A1 | 8/2003 | |
| EP | 1364667 A2 | 11/2003 | |
| EP | 1523360 A1 | 4/2005 | |
| EP | 1637181 A1 | 3/2006 | |
| EP | 1257321 B1 | 7/2008 | |
| EP | 2067496 A1 | 6/2009 | |
| EP | 2085104 A1 | 8/2009 | |
| EP | 2180459 A1 | 4/2010 | |
| EP | 2361648 A1 | 8/2011 | |
| GB | 2243552 A | 11/1991 | |
| GB | 2388033 A | 11/2003 | |
| GB | 2465389 A | 5/2010 | |
| JP | 2001-508648 A | 7/2001 | |
| JP | 2001-512038 A | 8/2001 | |
| JP | 2006-507060 A | 3/2006 | |
| JP | 50-14835 B2 | 8/2012 | |
| JP | 5-161712 B2 | 3/2013 | |
| RU | 2004256 C1 | 12/1993 | |
| RU | 2069584 C1 | 11/1996 | |
| RU | 2131748 C1 | 6/1999 | |
| RU | 2169584 C1 | 6/2001 | |
| WO | WO-86/01533 A1 | 3/1986 | |
| WO | WO-87/02671 A1 | 5/1987 | |
| WO | WO-90/01047 A1 | 2/1990 | |
| WO | WO-90/07861 A1 | 7/1990 | |
| WO | WO-91/03553 A1 | 3/1991 | |
| WO | WO-91/17271 A1 | 11/1991 | |
| WO | WO-92/01047 A1 | 1/1992 | |
| WO | WO-92/09690 A2 | 6/1992 | |
| WO | WO-92/15679 A1 | 9/1992 | |
| WO | WO-92/18619 A1 | 10/1992 | |
| WO | WO-92/20791 A1 | 11/1992 | |
| WO | WO-93/01288 A1 | 1/1993 | |
| WO | WO-93/06213 A1 | 4/1993 | |
| WO | WO-93/13819 A1 | 7/1993 | |
| WO | WO-93/19751 A1 | 10/1993 | |
| WO | WO-94/06476 A1 | 3/1994 | |
| WO | WO-94/08609 A1 | 4/1994 | |
| WO | WO-94/09839 A1 | 5/1994 | |
| WO | WO-94/13342 A1 | 6/1994 | |
| WO | WO-94/26333 A1 | 11/1994 | |
| WO | WO-97/29131 A1 | 8/1997 | |
| WO | WO 99/03529 | 1/1999 | |
| WO | WO-99/22789 A1 | 5/1999 | |
| WO | WO-99/22792 A1 | 5/1999 | |
| WO | WO-9943283 A1 | 9/1999 | |
| WO | WO-01/37908 A1 | 5/2001 | |
| WO | WO-0151123 A1 | 7/2001 | |
| WO | WO-01/62319 A2 | 8/2001 | |
| WO | WO-02/072636 A2 | 9/2002 | |
| WO | WO-03/039433 A1 | 5/2003 | |
| WO | WO-03/039633 A2 | 5/2003 | |
| WO | WO-03/077968 A2 | 9/2003 | |
| WO | WO-03/097133 A1 | 11/2003 | |
| WO | WO-03/099358 A2 | 12/2003 | |
| WO | WO-2004000397 A1 | 12/2003 | |
| WO | WO 2004000397 A1 * | 12/2003 | ............... A61M 5/32 |
| WO | WO-2004/016286 A2 | 2/2004 | |
| WO | WO-02/12502 A9 | 3/2004 | |
| WO | WO-2004/024211 A2 | 3/2004 | |
| WO | WO-2004041330 A2 | 5/2004 | |
| WO | WO-2004/047892 A1 | 6/2004 | |
| WO | WO-2004/060451 A1 | 7/2004 | |
| WO | WO-2004/067068 A1 | 8/2004 | |
| WO | WO-2005/002653 A1 | 1/2005 | |
| WO | WO-2005000206 A2 | 1/2005 | |
| WO | WO-2005/046765 A2 | 5/2005 | |
| WO | WO-2005/079889 A1 | 9/2005 | |
| WO | WO-2005/090836 A1 | 9/2005 | |
| WO | WO-2005/113039 A1 | 12/2005 | |
| WO | WO-2005/115508 A1 | 12/2005 | |
| WO | WO-2005/115509 A1 | 12/2005 | |
| WO | WO-2005/115510 A1 | 12/2005 | |
| WO | WO-2005/115511 A1 | 12/2005 | |
| WO | WO-2005/115512 A1 | 12/2005 | |
| WO | WO-2005/115513 A1 | 12/2005 | |
| WO | WO-2005/115516 A1 | 12/2005 | |
| WO | WO-2006/000785 A1 | 1/2006 | |
| WO | WO-2006/058061 A1 | 6/2006 | |
| WO | WO-2006/063015 A2 | 6/2006 | |
| WO | WO-2006057636 A1 | 6/2006 | |
| WO | WO-2006083876 A2 | 8/2006 | |
| WO | WO-2007056231 A2 | 5/2007 | |
| WO | WO-2007/126851 A2 | 11/2007 | |
| WO | WO-2008/005315 A2 | 1/2008 | |
| WO | WO-2008064092 A2 | 5/2008 | |
| WO | WO-2008091838 A2 | 7/2008 | |
| WO | WO-2009/040603 A1 | 4/2009 | |
| WO | WO-2009140251 A2 | 11/2009 | |
| WO | WO-2009/155277 A1 | 12/2009 | |
| WO | WO-2010/029054 A1 | 3/2010 | |
| WO | WO-2010046319 A1 | 4/2010 | |
| WO | WO-2010/056712 A1 | 5/2010 | |
| WO | WO-2010/127146 A1 | 11/2010 | |
| WO | WO-2011/014514 A1 | 2/2011 | |
| WO | WO-2011/014704 A2 | 2/2011 | |
| WO | WO-2011/075524 A1 | 6/2011 | |
| WO | WO-2011/133823 A1 | 10/2011 | |
| WO | WO-2012/129174 A1 | 9/2012 | |
| WO | WO-2012/135524 A1 | 10/2012 | |

OTHER PUBLICATIONS

Office Action issued in Chinese Application No. 2010105764136, dated Jul. 31, 2012.
International Search Report and Written Opinion issued in International Application No. PCT/US2012/029682, dated Jul. 27, 2012.
International Search Report and Written Opinion issued in International Application No. PCT/US2012/022432, dated Apr. 18, 2012.
International Search Report issued in International Application No. PCT/US2012/022433, dated Jul. 5, 2012.
Written Opinion issued in International Application No. PCT/US2012/022433, dated Jul. 5, 2012.

(56) References Cited

OTHER PUBLICATIONS

BD Preventis.TM., Shielding System for Prefilled Syringes, http://www.bd.com/pharmaceuticals/products/safety-engineered.asp, last accessed on Aug. 26, 2010.
Inquiry issued by the Russia Federal Intellectual Property Institute on Russian Patent Application No. 2006145501/14(049694), dated May 21, 2009.
International Search Report on International Patent Application No. PCT/GB2005/002487, dated Aug. 19, 2005.
Notice of Reasons for Rejection issued by the Japanese Patent Office on Japanese Patent Application No. 2007-517459, dated Aug. 24, 2010.
Office Action issued by the Mexican Patent Office on Mexican Patent Application No. PA/a/2006/015056, dated Jul. 28, 2010, with English translation.
Notification of Reexamination issued by the Chinese Patent Office on Chinese Patent Application No. 200580020958.6, dated Aug. 17, 2010.
Rejection Decision issued by the Chinese Patent Office on Chinese Patent Application No. 200580020958.6, dated Jun. 5, 2009.
First Office Action issued by the Chinese Patent Office on Chinese Patent Application No. 200580020958.6, dated Sep. 5, 2008.
Examiner's First Report issued by the Australian Patent Office on Australian Patent Application No. 2005256832, dated Feb. 22, 2010.
Communication pursuant to Article 94(3) EPC issued by the European Patent Office on European Patent Application No. 05 758 156.3-2320 dated Jan. 18, 2011.
Communication of a Notice of Opposition issued in European Application No. 04822031.3-1526, dated Jan. 6, 2010.
Communication pursuant to Article 96(2) EPC issued in European Application No. 04822031.3-1526, dated May 31, 2007.
Communication under Rule 112 EPC issued in European Application No. 04822031.3, dated Mar. 13, 2007.
International Search Report issued in International Application No. PCT/GB2005/002487, dated Aug. 19, 2005.
Written Opinion issued in International Application No. PCT/GB2005/002487, dated Dec. 23, 2006.
International Preliminary Report on Patentability issued in International Application No. PCT/GB2005/002487, dated Sep. 7, 2006.
International Search Report issued in International Application No. PCT/US2011/033504, dated Jul. 8, 2011.
Written Opinion issued in International Application No. PCT/US2011/033504, dated Jul. 8, 2011.
International Search Report issued in International Application No. PCT/US2007/015095, dated Sep. 11, 2008.
Written Opinion issued in International Application No. PCT/US2007/015095, dated Sep. 11, 2008.
International Preliminary Report on Patentability issued in International Application No. PCT/US2007/015095, dated Jun. 19, 2009.
International Search Report issued in International Application No. PCT/US2010/033012, dated Jul. 2, 2010.
Written Opinion issued in International Application No. PCT/US2010/033012, dated Jul. 2, 2010.
International Search Report issued in International Application No. PCT/US2010/060496, dated Feb. 16, 2011.
Written Opinion issued in International Application No. PCT/US2010/060496, dated Feb. 16, 2011.
International Search Report issued in International Application No. PCT/US2004/013278, dated May 30, 2005.
Written Opinion issued in International Application No. PCT/US2004/013278, dated Oct. 29, 2006.
International Preliminary Report on Patentability issued in International Application No. PCT/US2004/013278, dated Nov. 1, 2006.
Office Action issued in Russian Application No. 2006145501/14(049694), dated May 21, 2009.
Decision on Grant issued in Russian Application No. 2006145501/14(049694), dated Nov. 2, 2009.
Decision on Grant issued in Russian Application No. 2009102986/14(003862), dated Jun. 30, 2011.
Notice of Reasons for Rejection issued in Japanese Application No. 2007-517459, dated Mar. 8, 2011.
Office Action issued in Mexican Application No. PA/a/2006/015056, dated Jul. 28, 2010.
Office Action issued in Mexican Application No. PA/a/2006/015056, dated Apr. 1, 2011.
Reexamination Decision issued in Chinese Application No. 200580020958.6, dated Jun. 13, 2011.
Notification of Reexamination issued in Chinese Application No. 200580020958.6, dated Aug. 17, 2010.
Rejection Decision issued in Chinese Application No. 200580020958.6, dated Jun. 5, 2009.
Office Action issued in Chinese Application No. 200580020958.6, dated Sep. 5, 2008.
Office Action issued in Australian Application No. 2005256832, dated Apr. 18, 2011.
Office Action issued in Australian Application No. 2005256832, dated Feb. 22, 2010.
Examination Report issued in New Zealand Application No. 552340, dated Apr. 27, 2009.
Examination Report issued in New Zealand Application No. 552340, dated Aug. 12, 2010.
"Abbott Receives FDA Approval for New Humira Delivery Device," Press Release, dated Jun. 26, 2006 (color).
Notification of Provisional Rejection issued in Korean Application No. 10-2006-7026814, dated Jul. 19, 2011.
Correspondence from Dept. of Health & Human Services, Food and Drug Administration, to Robert Shaw/Owen Mumford, Inc. regarding Section 501(k) notification to market device, dated Nov. 10, 1999.
Correspondence from Dept. of Health & Human Services, Food and Drug Administration, to Robert Shaw/Owen Mumford, Inc. regarding Section 501(k) notification to market device, dated Mar. 6, 2000.
Owen Mumford drawing/schematic of the Abbott-Plunger AUTOject Mini, dated Mar. 25, 2002, Drawing No. P02 207.
Owen Mumford drawing/schematic of the Plunger-Miniject dated Mar. 30, 1993, Drawing No. P93.022.
Owen Mumford drawing/schematic of the Plunger-Miniject dated Mar. 30, 1993, Drawing No. AJ 358.
Owen Mumford drawing/schematic A of the Plunger-Miniject dated Sep. 5, 1997, Drawing No. AJ 654.
Owen Mumford drawing/schematic B of the Plunger-Miniject dated Sep. 5, 1997, Drawing No. AJ 654.
Office Action issued in Canadian Application No. 2,571,571, dated Oct. 24, 2011.
Office Action issued in Chinese Application No. 201010576413.6, dated Nov. 2, 2011.
International Preliminary Report on Patentability issued in International Application No. PCT/US2010/033012, dated Nov. 1, 2011.
U.S. Appl. No. 11/804,587, Not Published.
U.S. Appl. No. 11/824,516, Not Published.
U.S. Appl. No. 12/306,513, Not Published.
U.S. Appl. No. 11/786,444, Not Published.
U.S. Appl. No. 11/786,445, Not Published.
U.S. Appl. No. 11/880,433, Not Published.
U.S. Appl. No. 11/786,053, Not Published.
U.S. Appl. No. 11/788,312, Not Published.
U.S. Appl. No. 11/786,461, Not Published.
U.S. Appl. No. 11/818,510, Not Published.
U.S. Appl. No. 11/788,740, Not Published.
U.S. Appl. No. 12/130,831, Not Published.
U.S. Appl. No. 10/622,683, Not Published.
U.S. Appl. No. 10/623,318, Not Published.
U.S. Appl. No. 12/646,891, Not Published.
U.S. Appl. No. 12/859,181, Not Published.
U.S. Appl. No. 13/019,810, Not Published.
U.S. Appl. No. 13/019,872, Not Published.
U.S. Appl. No. 13/034,809, Not Published.
U.S. Appl. No. 29/383,882.
U.S. Appl. No. 13/092,102.
Decision of Final Rejection issued in Japanese Application No. 2007-517459, dated Jan. 10, 2012.
Notice of Rejection issued in Japanese Application No. 2009-518284, dated May 29, 2012.

(56) References Cited

OTHER PUBLICATIONS

Examination Report issued in Australian Application No. 2007269791, dated Jul. 30, 2012.
Notice of Rejection issued in Japanese Application No. 2011-196424, dated Jan. 29, 2013.
Invitation to Pay Additional Fees issued in International Application No. PCT/US2012/034683, dated Nov. 7, 2012.
Examination Report issued in Australian Application No. 2010331936, dated Nov. 12, 2012.
Examination Report issued in New Zealand Application No. 600069, dated Mar. 28, 2013.
International Preliminary Report on Patentability issued in PCT/US2010/060496, mailed Jun. 19, 2012.
International Search Report issued in International Application No. PCT/US2012/029682, mailed Jul. 27, 2012.
Office Action issued in Chinese Application No. 201080029621.2, dated Feb. 27, 2013.
Owen Mumford drawing/schematic of the Plunger—Autoject Mini dated May 9, 1997, Drawing No. AJ 654.
PCT International Search Report and Written Opinion Dated Jun. 26, 2013 for PCT/US2013/028619.
Summons to Attend Oral Proceedings pursuant to Rule 115(1) EPC issued in EP 04822031.1, dated Apr. 20, 2012.
Written Opinion issued in PCT/US2012/029682, mailed Jul. 27, 2012.
Search Report issued in European Application No. 13152833.3 mailed Jun. 7, 2013.
Examination Report issued in Australian Application No. 2011250802 mailed May 8, 2013.
Notice of Reasons for Rejection issued in Japanese Application No. 2012-108830 mailed Jun. 18, 2013.
Examination Report issued in Indian Application No. 80/DELNP/2007 mailed Jun. 21, 2013.
Search Report issued in European Application No. 13152831.7 mailed Jun. 7, 2013.

\* cited by examiner

AUTOMATIC INJECTION DEVICES

RELATED APPLICATIONS

The instant application is a continuation of U.S. patent application Ser. No. 13/072,289 filed on Mar. 25, 2011 which is a continuation of U.S. patent application Ser. No. 11/630,507 filed Jan. 7, 2008, which is a '371 of PCT Patent Application No. PCT/GB2005/002487, filed Jun. 23, 2005, which claims priority to United Kingdom Patent Application No.: 0414054.7 filed on Jun. 23, 2004. The entire contents of each of the above documents are herein incorporated by reference in their entirety.

BACKGROUND

There are various forms of automatic injection device which when operated cause the needle of a syringe to be moved forwardly so that it projects from a protective housing prior to actuation of the syringe to express a dose of liquid through the needle. It is important to try to ensure that the syringe is moved bodily forward to expose the needle before the liquid charge is pressurised so that dribbling from the needle does not occur before the actual injection takes place. It is an object of this invention to provide a mechanism which operates in this desired manner.

SUMMARY

According to the invention there is provided an injection device for causing a dose of liquid to be ejected from the needle at one end of a syringe located within a housing of the device, the syringe being movable by a plunger, upon release of an actuating bias member at one end of the housing, to move the syringe, from a first position wherein the needle is shrouded by the housing, to a second position wherein the needle projects from the other end of the housing, the plunger being in the form of a rod with a longitudinally centrally located flexible projecting portion which, prior to release of said actuating bias member, is situated beyond the other end of the syringe, such that a primary movement of the plunger, under the bias of the actuating bias member, will cause the projecting portion to bear against the other end of the syringe such that the syringe is moved from said first to said second position, whereupon arresting of further movement of the syringe, results in the flexible portion collapsing inwardly so that it enters the syringe, thus enabling the plunger to move by a secondary movement, within the syringe, into contact with and to act upon a plug to compress the liquid within the syringe and cause expression of the liquid through the syringe needle.

With such an arrangement, the projecting portion will remain in its projecting position (in order to move the syringe from the first to the second position) until the force increases to such an extent which allows the projecting portion to collapse inwardly so that the plunger can then move within the syringe to cause the liquid to be expressed through the syringe.

The projecting portion can comprise one or more flexible elbows projecting beyond the normal circumference of the rod, but compressible into said circumference. This could be in the form of two elbows defined either side of a longitudinal slit in the rod. The elbows could be pre-formed as a pair of arms either side of the longitudinal slit between upper and lower solid portions of the rod.

Preferably the injection device will contain a return bias member acting between the syringe housing and the other end of the syringe to hold the syringe retracted within the housing until the actuating bias member is released. One or more of the bias members provided within the housing can be in the form of a coil spring.

BRIEF DESCRIPTION OF THE DRAWINGS

The invention may be performed in various ways and a preferred example thereof will now be described, with reference to the accompanying diagrammatic drawings, in which.

DESCRIPTION

Figure 1:
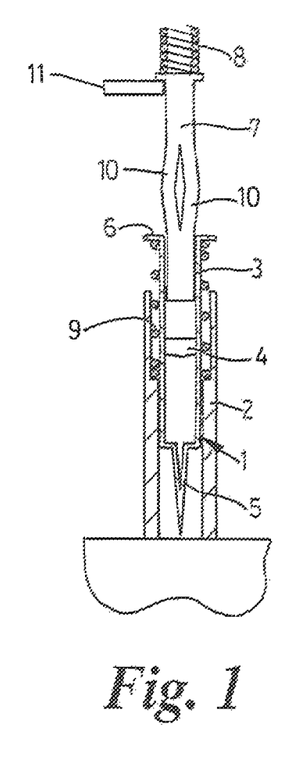
FIG. 1 is a sectional view through an injection device of this invention prior to use.

The injection device shown in the drawings comprises a syringe 1 located within a protective housing 2. The syringe comprises a 3 incorporating a liquid dose held in place by a bung 4 and having a needle 5 through which the dose can be ejected by applying pressure to the bung 4. The 3 has an enlarged head 6. A plunger 7 is biased forwardly by a coil spring 8, but is held back in a latched position (FIG. 1) until such time as a trigger shown schematically at 11 is actuated to release the plunger and the spring 8. Prior to use the syringe 1 is held retracted in the housing 2 by a coil spring 9.

Figure 2:
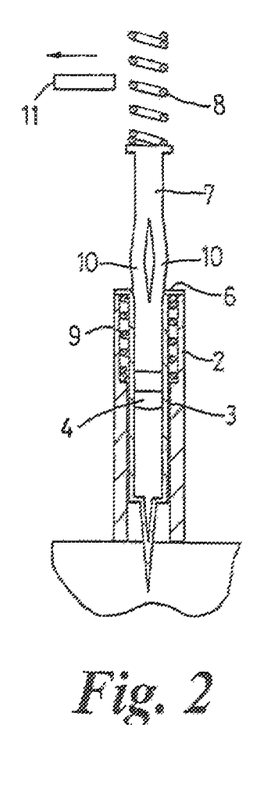
FIGS. 2 and 3 are similar views showing successive stages of operation of the injection member.
Figure 3:
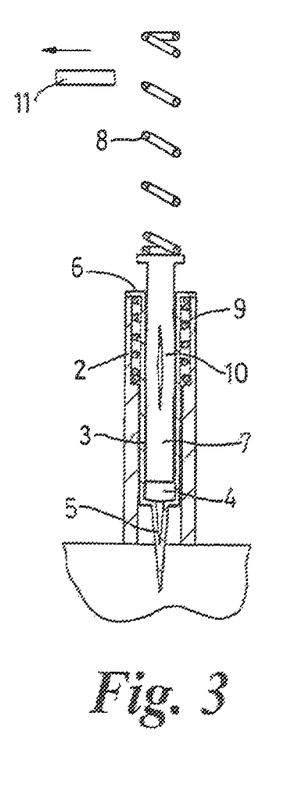

It will be seen that the plunger 7 is in the form of a rod having a central portion which defines a pair of projecting elbows 10. These can be pre-formed as part of a moulded plunger 7. The projecting elbow portions 10 are flexible so that they can be moved inwardly to cause that portion of the rod to adopt a circumference similar to that of the rest of the rod. As can be seen in FIG. 2, when the plunger is released and biased by the spring 8 the expanded region formed by the elbows 10 rests against the head 6 of the 3 and the force provided is sufficient to compress the spring 9 until such time as the head 6 abuts the top of the housing 2, whereupon further movement of the 3 is arrested. The continual bias created by the spring 8 then causes the elbows 10 to be 20 compressed inwardly as they enter into the interior of the 3. With the elbows 10 in the collapsed state, the plunger can then move relatively easily within the 3 so as to act upon the bung 4 and thus cause the contents of the syringe to be ejected through the needle 5.

The illustrated configuration of the plunger 7 provides several technical advantages. It can be moulded integrally. Also the collapsing movement of the projecting elbows provides an arrangement which can provide a suitable injection force to cause the needle to enter the skin to a suitable depth, but then provide a relatively low drag against the inner wall of the syringe container so that the major portion of the thrust of the spring for the remainder of its stroke is applied to the bung 4. It will be appreciated that other configurations of collapsing projection could be used in place of the collapsing elbows.

What is claimed is:
1. An injection device, comprising:
a housing;
a syringe slideably mounted within the housing for movement between a shrouded retracted position relative to the housing and an extended injecting position relative to the housing;
a movable bung slideably mounted in the syringe and moveable to expel a liquid dose through a needle couplable at a distal end of the syringe;

a plunger having a distal end operable to move the bung and to transmit an expulsion force thereto, the plunger being in the form of a rod including:
    an upper solid portion having a circular cross-sectional profile,
    a lower solid portion having a distal end operable to move the bung and to transmit an expulsion force thereto, the lower solid portion having a first circular circumference, and
    a projecting portion comprising two flexible elbows on either side of a central void extending along a central axis of the plunger between the upper and lower solid portions, wherein the flexible elbows project outwardly from the central void when the projecting portion is in a first projecting position, wherein the flexible elbows are inwardly collapsible toward the central void when the projecting portion is in a second collapsed position; and
an actuating bias spring operable to drive the plunger to move the syringe from the shrouded retracted position relative to the housing to the extended injecting position relative to the housing, and to move the plunger forwardly within the syringe to act upon the bung to transmit the expulsion force thereto in order to expel the liquid dose from the syringe through the needle.

2. The injection device of claim 1, wherein the flexible elbows are formed by bifurcation of opposite ends of the upper and lower solid portions.

3. The injection device of claim 1, wherein the central void is a longitudinal slit in the rod.

4. The injection device of claim 1, wherein the central void has an elongated oval cross-sectional profile extending along the central axis of the plunger, and wherein the central void has a first larger width when the projecting portion is in the first projecting position and a second smaller width when the projecting portion is in the second collapsed position.

5. The injection device of claim 1, further comprising:
    a return bias member acting between the housing and a proximal end of the syringe to hold the syringe retracted within the housing until the actuating bias member is released.

6. The injection device of claim 5, wherein one or more of the bias members provided within the housing is in the form of a coil spring.

7. The injection device of claim 1, wherein the housing is held fixed at an injection site and wherein the syringe moves within and relative to the housing during an injection.

8. The injection device of claim 1, wherein the plunger is integrally molded.

9. A syringe assembly, comprising:
a syringe couplable to a needle at a distal end;
a bung slideably mounted in the syringe; and
a plunger comprising:
    an upper solid portion having a circular cross-sectional profile,
    a lower solid portion having a distal end operable to move the bung and to transmit an expulsion force thereto, the lower solid portion having a first circular circumference, and
    a projecting portion comprising two flexible elbows on either side of a central void extending along a central axis of the plunger between the upper and lower solid portions, wherein the flexible elbows project outwardly from the central void when the projecting portion is in a first projecting position, wherein the flexible elbows are inwardly collapsible toward the central void when the projecting portion is in a second collapsed position, and wherein the central void is a longitudinally extending slit.

10. The syringe assembly of claim 9, wherein the syringe is slideably mountable within a housing for movement between a first position relative to the housing in which the needle is shrouded by the housing and a second position relative to the housing in which the needle projects from the housing.

11. The syringe assembly of claim 10, wherein the projecting portion of the plunger is configured to drive the syringe from the first position relative to the housing to the second position relative to the housing such that the needle projects from the housing.

12. The syringe assembly of claim 10, wherein movement of the plunger, upon release of an actuating bias member in an automatic injection device, causes the projecting portion to bear against an enlarged head of the syringe in the automatic injection device to drive the syringe from the first position relative to the housing to the second position relative to the housing.

13. The syringe assembly of claim 12, wherein, when in the second collapsed position, the projecting portion collapses inwardly so that it enters the syringe, wherein the collapse of the projecting portion enables the plunger to move within the syringe to compress a liquid dose within the syringe.

14. The syringe assembly of claim 9, wherein the flexible elbows are formed by bifurcation of opposite ends of the upper and lower solid portions.

15. The syringe assembly of claim 9, wherein the projecting portion of the plunger is in the first projecting position prior to entering the syringe and wherein the projecting portion is in the second collapsed position inside the syringe for applying the expulsion force to the bung.

16. The syringe assembly of claim 9, wherein a housing of an injection device is held fixed at an injection site and wherein the syringe moves within and relative to the housing during an injection.

17. The syringe assembly of claim 9, wherein the plunger is integrally molded.

\* \* \* \* \*

UNITED STATES PATENT AND TRADEMARK OFFICE
CERTIFICATE OF CORRECTION

| | | |
|---|---|---|
| PATENT NO. | : 8,668,670 B2 | |
| APPLICATION NO. | : 13/443384 | |
| DATED | : March 11, 2014 | |
| INVENTOR(S) | : Stephen Bicknell et al. | |

It is certified that error appears in the above-identified patent and that said Letters Patent is hereby corrected as shown below:

On the Title Page, Item (54) and in the Specification, Column 1, Line 1, In the Title:

Replace "AUTOMATIC INJECTION DEVICES" with --IMPROVEMENTS RELATING TO AUTOMATIC INJECTION DEVICES--.

Signed and Sealed this
Fourteenth Day of October, 2014

Michelle K. Lee
*Deputy Director of the United States Patent and Trademark Office*